(12) United States Patent
Michelson

(10) Patent No.: US 6,827,740 B1
(45) Date of Patent: Dec. 7, 2004

(54) SPINAL IMPLANT SURFACE CONFIGURATION

(76) Inventor: Gary K. Michelson, 438 Sherman Canal, Venice, CA (US) 90291

( * ) Notice: Subject to any disclaimer, the term of this patent is extended or adjusted under 35 U.S.C. 154(b) by 0 days.

(21) Appl. No.: 09/457,228

(22) Filed: Dec. 8, 1999

(51) Int. Cl.$^7$ .................................................. A61F 2/44
(52) U.S. Cl. .................................................. 623/17.11
(58) Field of Search ........................ 623/17.11, 17.15, 623/22.32, 23.26, 23.29, 23.31, 23.5, 20.17

(56) References Cited

U.S. PATENT DOCUMENTS

| | | | |
|---|---|---|---|
| 4,349,921 A | | 9/1982 | Kuntz |
| 4,834,757 A | | 5/1989 | Brantigan |
| 4,865,603 A | | 9/1989 | Noiles |
| 4,944,763 A | * | 7/1990 | Willert et al. .................. 623/23 |
| 5,522,899 A | | 6/1996 | Michelson |
| 5,553,446 A | | 9/1996 | Oehy et al. |
| 5,593,409 A | | 1/1997 | Michelson |
| 5,609,635 A | | 3/1997 | Michelson |
| 5,683,464 A | | 11/1997 | Wagner et al. |
| 5,755,799 A | | 5/1998 | Oehy et al. |
| 5,860,973 A | | 1/1999 | Michelson |
| 5,899,941 A | * | 5/1999 | Nishijima et al. ............. 623/17 |
| 6,174,334 B1 | * | 1/2001 | Suddaby ................... 623/17.11 |
| 6,258,125 B1 | * | 7/2001 | Paul et al. ................ 623/17.11 |
| 6,482,233 B1 | | 11/2002 | Aebi et al. |

* cited by examiner

Primary Examiner—Bruce E Snow
(74) Attorney, Agent, or Firm—Martin & Ferraro, LLP

(57) ABSTRACT

The present invention is a specialized implant having opposed surfaces for engaging each of the vertebral bodies adjacent a disc space into which the implant is implanted. The surface comprises arrayed projections having at least one forward facing facet directed at least in part toward the leading end of the implant and at least one rearward portion directed at least in part toward the opposite trailing end of the implant. Each of the forward facet and rearward portion has a length and a slope. The length of the forward facet is longer than the length of the rearward facet. The slope of the rearward facet is steeper than the slope of the forward facet. The surface projections also have opposed side facets directed generally toward the sides of the implant. The side facets are located between the forward facet and rearward facet and converge toward each other in a direction away from the base of the surface projections. The surface may also include projections having left and right forward side facets and a rearward facet. The surface further may include projections having left and right rearward side facets and a forward facet.

176 Claims, 9 Drawing Sheets

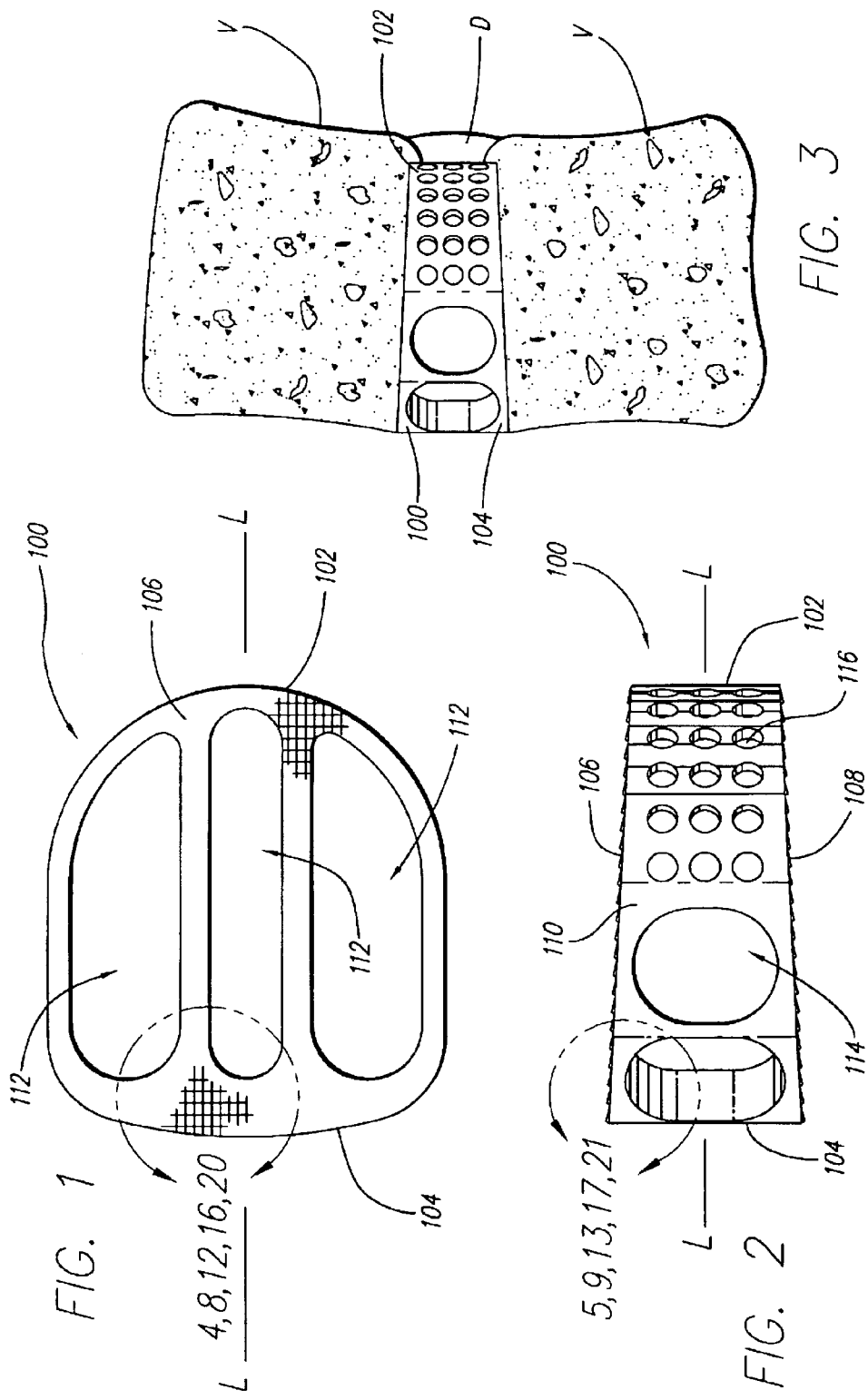

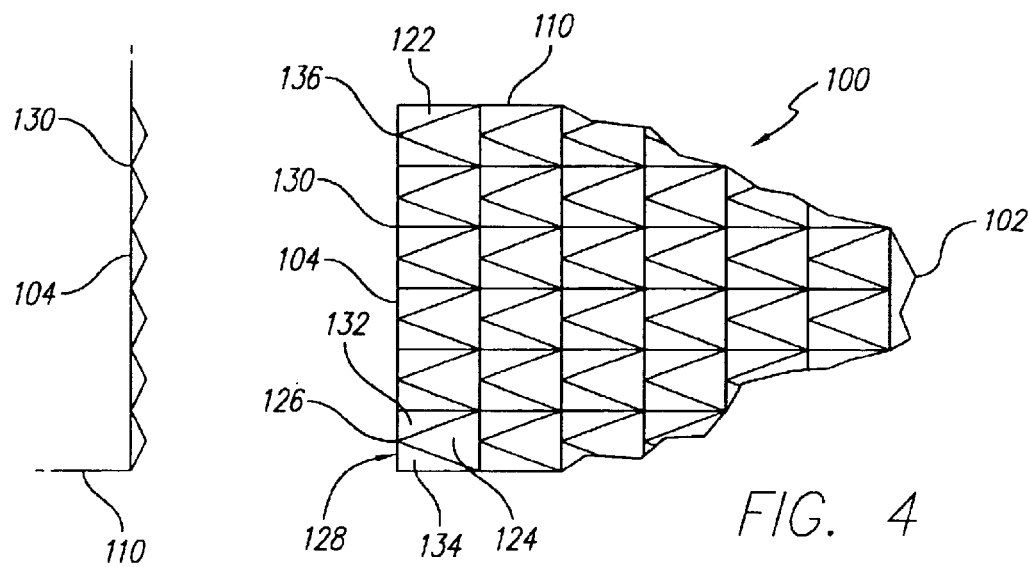
FIG. 6
FIG. 4
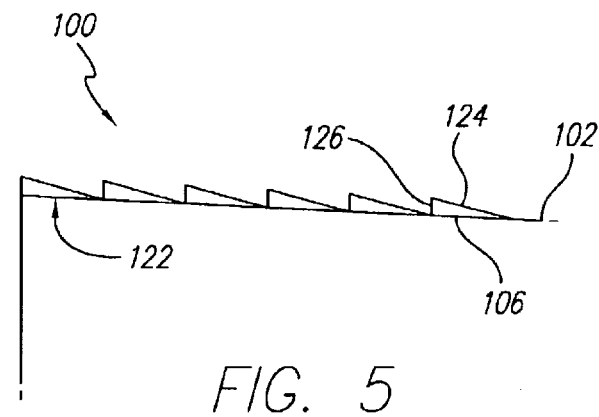
FIG. 5
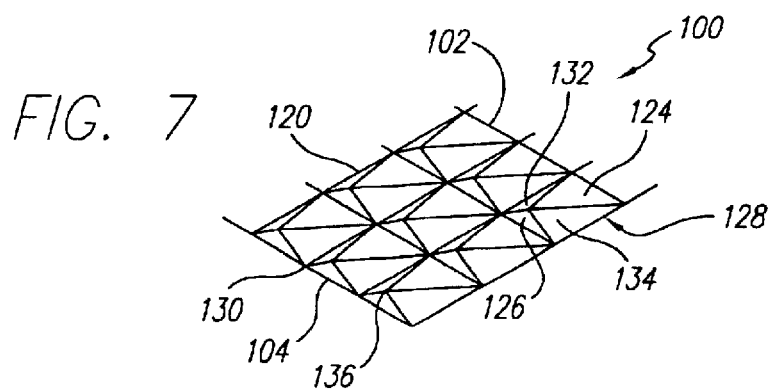
FIG. 7

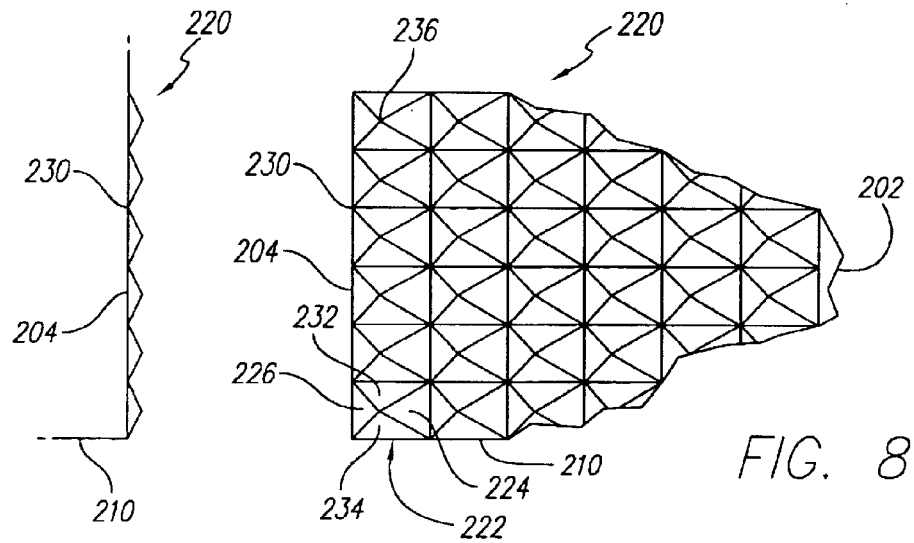
FIG. 10
FIG. 8
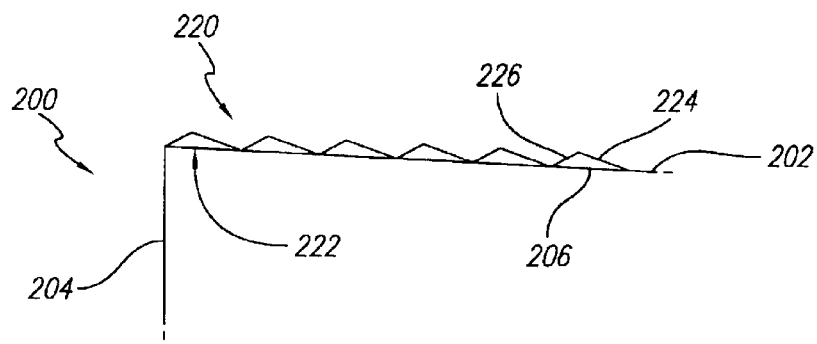
FIG. 9
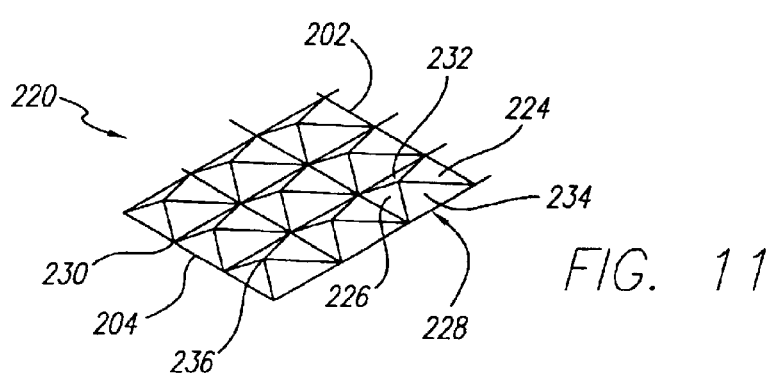
FIG. 11

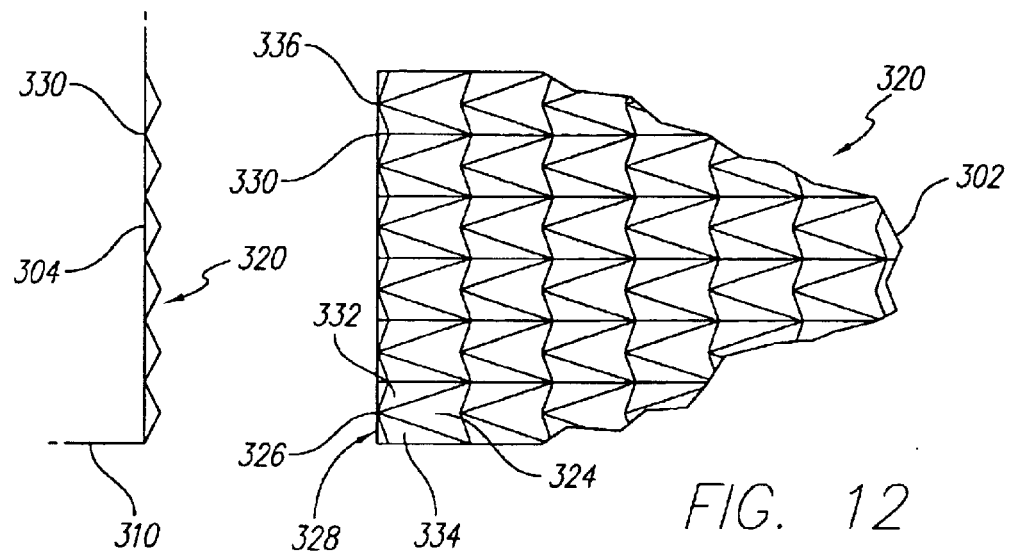
FIG. 12
FIG. 14
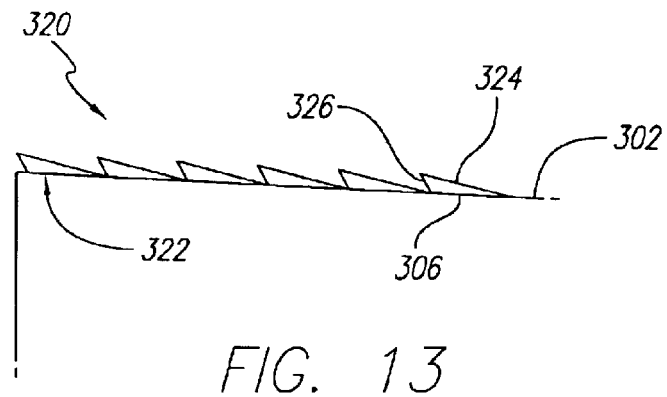
FIG. 13
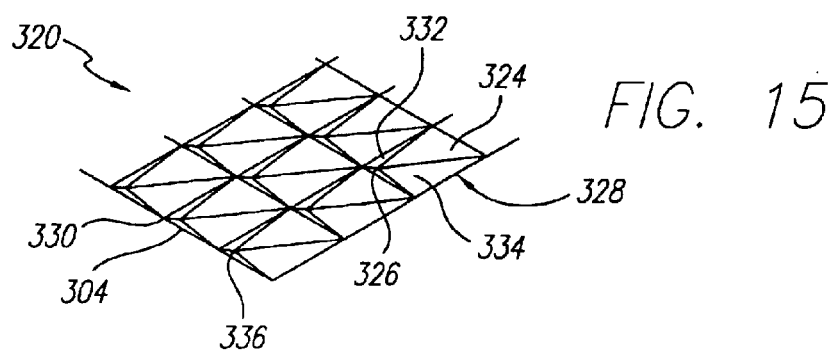
FIG. 15

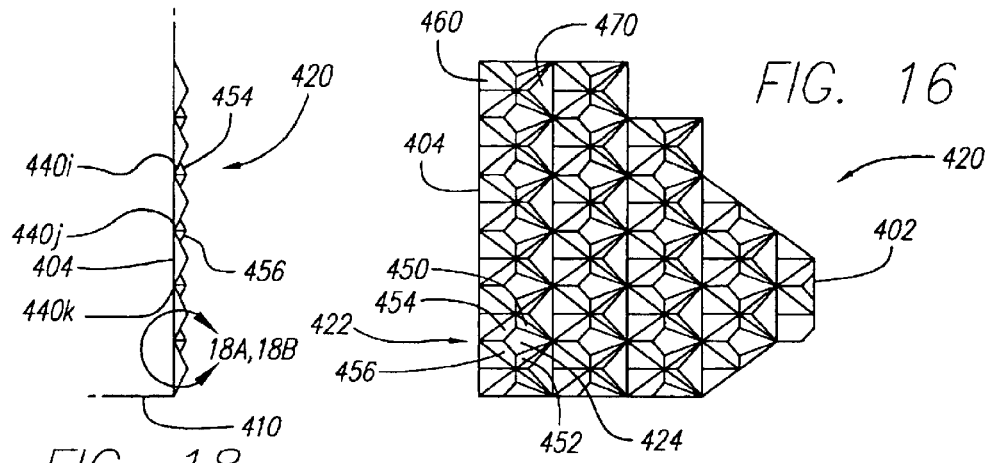
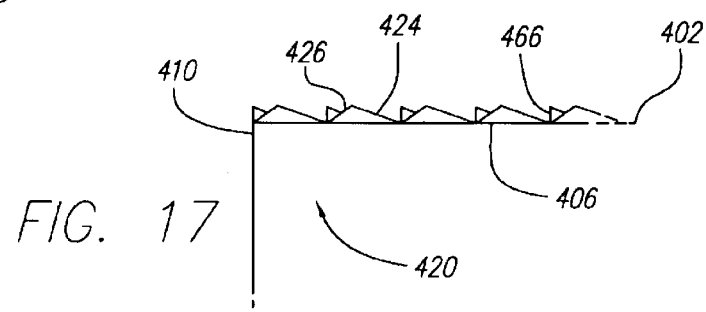
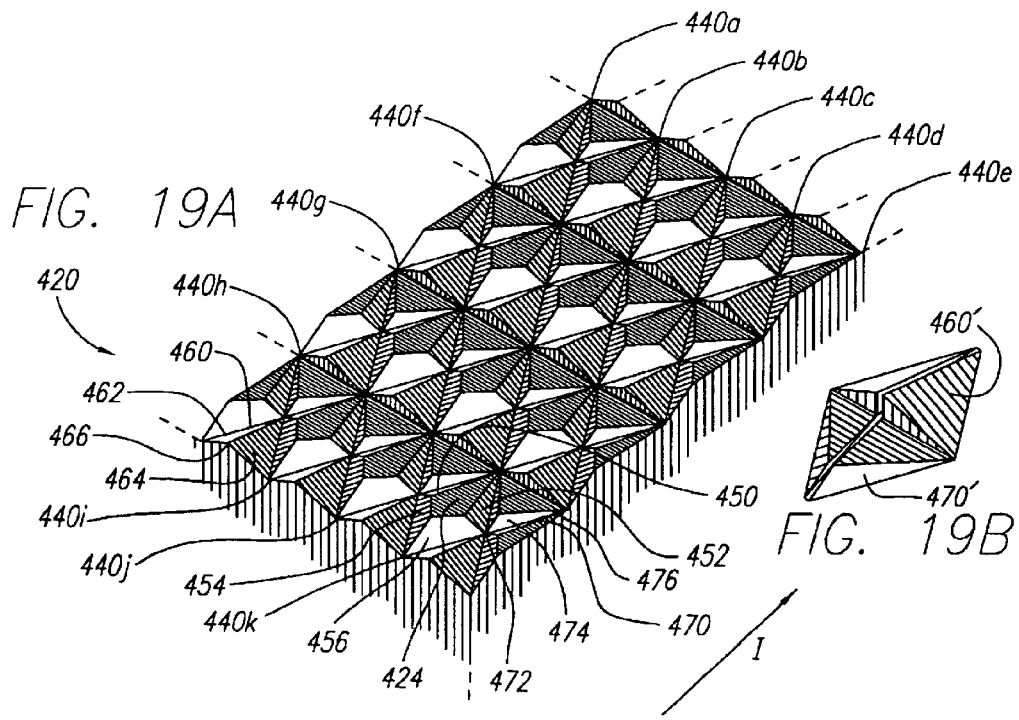

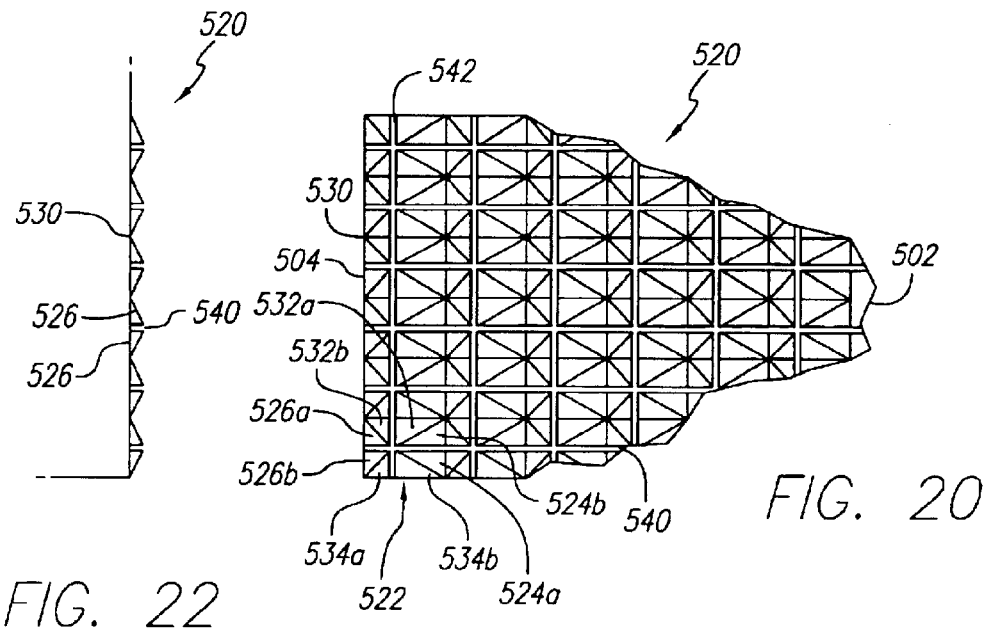
FIG. 20
FIG. 22
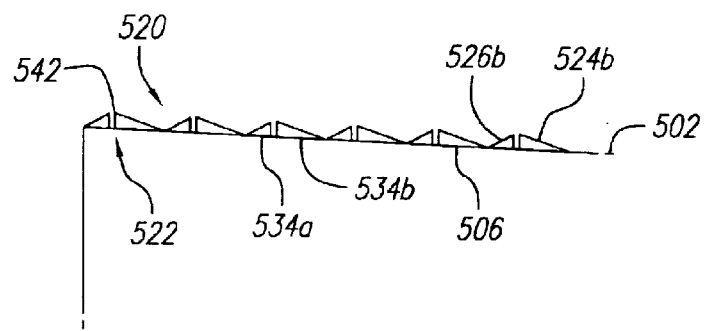
FIG. 21
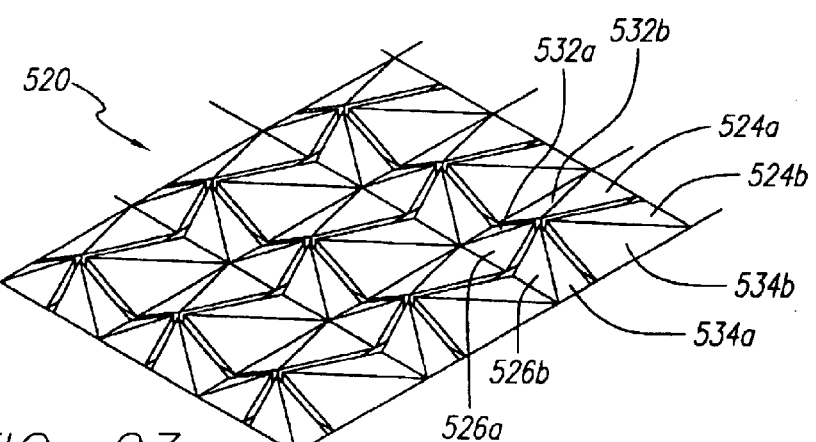
FIG. 23

SPINAL IMPLANT SURFACE CONFIGURATION

BACKGROUND OF THE INVENTION

Description of the Invention

The present invention relates to interbody spinal implants for placement between adjacent vertebral bodies of a human spine, and more specifically to a specialized surface for such interbody implants, for engaging the adjacent vertebral bodies. Vital to the functioning of all interbody spinal implants is their ability to remain properly located within the spine after installation. In U.S. Pat. Nos. 5,593,409 and 5,609,635, Michelson described the use of surface roughenings, such as knurling or ratcheting on the opposed upper and lower vertebral body engaging surfaces of interbody spinal fusion implants. Knurling has been particularly beneficial for increasing the grip of the implant surface to the adjacent vertebral bodies in a rather uniform manner without a directional bias. Spinal implants have a propensity to move in a particular direction, which is opposite to their path of insertion, because this is the path of least resistance. Such propensity to move is further increased when the opposed upper and lower vertebral body engaging surfaces are in angular relationship to each other, such that they are spaced further apart at the implant's trailing end than at the implant's leading end. In such circumstances where it is desirable then to gain stability in resistance to a particular direction of movement of the interbody spinal implant, the use of a plurality of forward facing ratchetings on the implant's vertebral body engaging surfaces has been preferable to the previously described knurling for that purpose.

The term "ratcheting" as used herein is defined as a plurality of angular teeth or ridges or protrusions projecting from the surface of an implant to resist motion of the implant at least in one direction. The phrase "forward facing ratchetings" as used herein is defined as a ratcheting having at least one forward facing facet having a length greater than a rearward facing facet and an angle from the implant surface from which the forward facing facet arises that is less steep than the angle of the rearward facet. On an implant surface, forward facing ratchetings facilitate the insertion of the implant in one direction and after insertion, resisting movement of the implant in a direction opposite to the direction of insertion. An example of forward facing ratchetings of the prior art is shown in partial fragmentary view in FIGS. 24A and 24B, generally referred to by the reference numeral 50.

Knurled surfaces of the related art provide some stability in all directions, but lack the ability to resist a particular direction of motion preferentially. The above-described ratcheted surface best resists motion in a particular direction. There exists a need for an improved interbody spinal implant surface configuration, wherein the opposed upper and lower vertebral body engaging surfaces of the implant are configured to be resistant to implant movement in all directions, and preferentially or in particularly in one direction.

SUMMARY OF THE INVENTION

The present invention relates to interbody spinal implants having a specialized surface configuration on the opposed exterior surfaces adapted for engaging the vertebral bodies adjacent a disc space into which the interbody implant is to be implanted. Such an implant surface configuration has utility with a wide variety of shapes of interbody spinal implants where enhanced skeletal fixation is desired. Such an implant surface configuration can provide for enhanced stability, increased surface area, and a surface for the delivery of fusion promoting substances other than bone. In a preferred embodiment, the implant surface can provide for resisting motion in all directions, and particularly in at least one direction, such as counter to the direction of insertion of the implant.

While various embodiments of the present invention are presented by way of example only and not limitation, common to each of them is that the surface configuration incorporates a plurality of spatially integrated surface projections having at least one forward facing facet directed at least in part toward the leading end of the implant and at least one rearward portion directed at least in part toward the opposite trailing end of the implant. By way of example and not limitation, the rearward portion may be a facet, a line, or an edge of the rearward aspect of the surface projection formed where two facets come together. Each of the forward and rearward facets have a length and a slope. The length of the forward facet is longer than the length of the rearward facet. The slope of the rearward facet is steeper than the slope of the forward facet. In various embodiments, the surface projections also have opposed side facets directed generally toward the sides of the implant. The side facets are located between the forward facet and rearward facet and may converge toward each other in a direction away from the base of the surface projections. The surface comprises multifaceted ratcheted projections that are organized in geometrically disposed fields or arrays which are at a minimum located on at least a portion of the opposed vertebral body engaging surfaces of the implant. From the teachings disclosed herein, it is appreciated that the surface projections can be geometrically arranged in a pattern wherein at least a portion of the projection is aligned along a longitudinal, horizontal, diagonal, or curved line. The upper and lower surfaces of the implant can be at least in part arcuate or planar and can converge along a portion or all of the length of the implant.

In various preferred embodiments of the present invention, the rearward facets of the surface projections can be perpendicular or at angles greater or less than 90 degrees to at least one of the upper or lower surfaces of the implant from which the projections arise. The opposed side facets of the surface projections can have at least a first portion in a plane at an angle to the longitudinal axis of the implant. The opposed side facets can intersect each other, and can converge to form a peak at the top of each of the surface projections. The peaks can be aligned along lines that are perpendicular, parallel, or diagonal to the longitudinal axis of the implant. The surface projections can be cleaved such as by longitudinal and/or horizontal cuts to increase the number of exposed sides of the projections and thus increase the available surface area to contact and engage the bone of the adjacent vertebral bodies and increase the number of recessed areas to contain fusion promoting substances. Alternatively, the peaks of each surface projection can be cleaved, truncated, or flattened at least in part.

The surface projections can include a left forward side facet and a right forward side facet directed toward the leading end and sides, respectively, of the implant. Similarly, the surface projections can include a left rearward side facet and a right rearward side facet directed toward the trailing end and sides, respectively, of the implant. The side facets of adjacent surface projections can be spaced apart to define a groove therebetween. A plurality of adjacent surface projections can be spaced apart to form a plurality of grooves that can be parallel or at an angle to the longitudinal axis of the implant, wherein the angle can be less than 90 degrees. The grooves can have a horizontal cross section that is a V-shape, U-shape, or a box-like shape, for example.

Sequential projections can be positioned on an implant wherein each surface projection has forward facing facets facing the same direction, such that consecutive projections are oriented forward facing facet to rearward facing facet. The lower most portion of the slope of the forward facing facet of a first surface projection in a sequence can be coincident with the rearward facet of the next surface projection in the sequence. Alternatively, the forward facet of a first surface projection and the rearward facet of the next surface projection in a sequence can be spaced apart and the space can be at least in part flat, curved, or any other surface contour suitable for the intended use. The surface projections can be oriented relative to one another to form fields or arrays that further can be geometrically disposed relative to one another, preferably in a pattern wherein at least a portion of the projection is aligned along a longitudinal, horizontal, diagonal, or curved line.

The surface configuration of the present invention can be formed by casting, machining, or any other techniques known to one of ordinary skill in the art. The present surface configuration may readily be machined by milling the implant surface from side to side, across the upper and lower vertebral body engaging surfaces, to form ratchetings generally disposed perpendicular to the long axis of the implant and generally formed facing to the insertion end of the implant. The ratchetings may be cross machined with an angled cutting face to form grooves passing through the ratchetings. For example, a milling machine having a cutting tool, with a V-shaped profile, can be run through the plurality of ratchetings parallel to the longitudinal axis of the implant to form the above-described surface. In a preferred embodiment, the V-shaped cutting tool of the milling machine has opposed cutting faces with an angle of approximately 90 degrees to each other, which faces are each at a 45-degree angle to the plane of the surfaces being machined. Without departing from the scope of the present invention, the angle of the cutting faces can be more or less than 90 degrees, and the angle of the cutting face to the surface to be cut can be more or less than 45 degrees. It is appreciated that rather than the cutting element being run parallel to the longitudinal axis of the implant, the cutting element could be run at some other angle. By way of example only and not limitation, this angle could be at 45 degrees to the longitudinal axis of the implant and to the projections. Each surface projection could then be formed by a cutter crossing in two passes to form two grooves at a 90 degree angle to each other.

The surface of the present invention for engaging each of the adjacent vertebral bodies may be incorporated into various types of spinal implants. Such spinal implants may be for the purpose of achieving interbody spinal fusion, or for stabilizing a device to space apart and allow motion between the adjacent vertebral bodies. Such spinal implants may comprise any artificial or naturally occurring material appropriate for the intended purpose. Such materials would include, but are not limited to, implant quality metals, including, but not limited to, titanium and its alloys, surgical grade plastics and plastic composites which may or may not be bioresorbable, ceramics, and cortical bone. Some examples of interbody spinal implants that may benefit from the present teaching, include but are not limited to the following patents and applications by Michelson which are incorporated by reference herein: U.S. Pat. Nos. 5,015,247; 5,522,899; 5,593,409; 5,609,635; 5,860,973; and application Ser. No. 08/480,904.

BRIEF DESCRIPTION OF THE DRAWINGS

FIG. 2 is a side elevation view of the spinal implant of FIG. 1.

FIG. 3 is a side elevation view of the interbody spinal implant of FIG. 1 installed in an implantation site formed across the disc space between two adjacent vertebral bodies of the spine shown in partial cross-section.

FIG. 4 is an enlarged fragmentary top plan view of an implant surface of one embodiment of the present invention from a view taken along area 4 of FIG. 1.

FIG. 5 is a fragmentary side elevation view of the implant surface of FIG. 4 from a view taken along area 5 of FIG. 2.

FIG. 6 is a fragmentary end elevation view of FIG. 4.

FIG. 7 is a fragmentary perspective view of the implant surface of FIG. 4.

FIG. 8 is an enlarged fragmentary top plan view of a second embodiment of the implant surface of the present invention from a view taken along area 8 of FIG. 1.

FIG. 9 is a fragmentary side elevation view of the implant surface of FIG. 8 from a view taken along area 9 of FIG. 2.

FIG. 10 is a fragmentary end view of the implant surface of FIG. 8.

FIG. 11 is a fragmentary perspective view of the implant surface of FIG. 8.

FIG. 12 is an enlarged fragmentary top plan view of a third embodiment of the implant surface of the present invention from a view taken along area 12 of FIG. 1.

FIG. 13 is a fragmentary side elevation view of the implant surface of FIG. 12 from a view taken along area 13 of FIG. 2.

FIG. 14 is a fragmentary end view of FIG. 12.

FIG. 15 is a fragmentary perspective view of the implant surface of FIG. 12.

FIG. 16 is an enlarged fragmentary top plan view of a fourth embodiment of the implant surface of the present invention from a view taken along area 16 of FIG. 1.

FIG. 17 is a fragmentary side elevation view of the implant surface of FIG. 16 from a view taken along area 17 of FIG. 2.

FIG. 18 is a fragmentary end view of FIG. 16.

FIG. 19A is an enlarged fragmentary perspective view of the implant surface of FIG. 16.

FIG. 19B is an enlarged fragmentary perspective view of a variation on the second and third surface projections of the fourth embodiment of the implant surface of the present invention with a cleave therethrough.

FIG. 20 is an enlarged fragmentary top plan view of a fifth embodiment of the implant surface of the present invention from a view taken along area 20 of FIG. 1.

FIG. 21 is a fragmentary side elevation view of the implant surface of FIG. 20 from a view taken along line 21 of FIG. 2.

FIG. 22 is a fragmentary end view of FIG. 20.

FIG. 23 is an enlarged fragmentary perspective view of the implant surface of FIG. 20.

DETAILED DESCRIPTION OF THE DRAWINGS

Figure 1A:
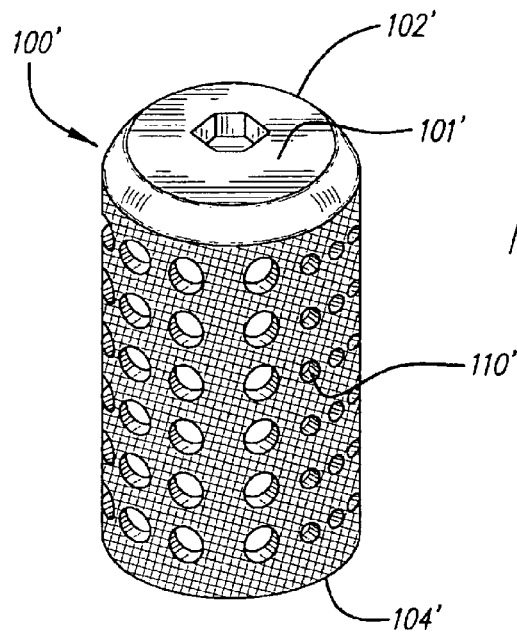
FIG. 1A is a perspective view of an implant having arcuate surfaces and an end cap in accordance with an embodiment of the present invention.

As shown in FIGS. 1–7, an interbody spinal implant 100 has a leading end 102, a trailing end 104, an upper surface 106, a lower surface 108, and a side wall 110 between upper and lower surfaces 106, 108. Upper and lower surfaces 106, 108 may converge from trailing end 104 to leading end 102 along a longitudinal axis L of implant 100 as shown, or may diverge, be parallel, or any combination thereof. Upper and lower surfaces 106, 108 are configured to be placed against and in contact or engagement with the bone of vertebral bodies V of two adjacent vertebrae adjacent disc D of the human spine. Upper and lower surfaces 106,108 and side wall 110 may include large and/or small openings 112, 114, and 116, respectively, to permit bone growth into and through implant 100. Upper and lower surfaces 106,108 of implant 100 can be generally planar as shown in the figures, or can be opposed arcuate surfaces as shown and described in U.S. Pat. No. 5,593,409, incorporated herein by reference, or any other configuration suitable for the desired use.

As shown in detail in FIGS. 4–7, at least a portion of upper and lower surfaces 106, 108 of implant 100 have a surface configuration generally referred to by the numeral 120. In accordance with a first embodiment of the present invention, surface configuration 120 includes surface projections 122 configured to facilitate insertion of implant 100 into an implantation site while resisting expulsion of implant 100 in a direction opposite to the direction of insertion. Each of surface projections 122 has an angled forward facet 124 directed at least in part toward leading end 102 of implant 100 and a rearward facet 126 directed at least in part toward trailing end 104 of implant 100. Forward facet 124 has a length greater than the length of rearward facet 126. Rearward facet 126 has a slope that is steeper than the slope of forward facet 124. In this embodiment, the base of rearward facet 126 forms an angle of approximately 90 degrees with respect to upper and/or lower surfaces 106, 108 of implant 100. It is appreciated that the angle of the base of rearward facet 126 with respect to upper and/or lower surfaces 106, 108 of implant 100 may be perpendicular to, greater than perpendicular to, or less than perpendicular to the base of the surface where the facet arises. Forward facet 124 forms an angle in the range of approximately 10 to 60 degrees, with 25–45 degrees being preferred, with respect to upper and/or lower surfaces 106, 108. Each one of surface projections 122 also has a left side facet 132 and a right side facet 134 directed toward the sides of implant 100.

In this embodiment of surface configuration 120, a plurality of surface projections 122 are spaced apart laterally (side to side) by longitudinal grooves 130 formed along the longitudinal axis L of implant 100. In one embodiment, longitudinal grooves 130 have a V-shaped horizontal cross-section. The lower most portions of left and right side facets 132, 134 of consecutive side-by-side projections 122 can be coincident with each other or may be spaced apart, any space therebetween can be at least in part flat, curved, sloped or otherwise configured. Each surface projection 122 has left and right side facets 132, 134 that converge to form a high point or peak 136 at the top of each surface projection 122. Each peak 136 can be aligned along lines that are perpendicular, parallel, and/or diagonally oriented to longitudinal axis L of implant 100. The left and right side facets 132,134 resist side-to-side motion of implant 100 after it is inserted into the implantation space. Peaks 136 engage the bone of vertebral bodies V adjacent to implant 100 in the implantation site. It is appreciated that in a variation of the present invention, the peaks may be modified such as to be truncated or cut off to have a broader rather than sharper upper most surface. Moreover, the peaks can be cleaved in one or more directions so as to increase the surface area useful for engaging the bone of the vertebral bodies. The relieved areas of the cleaved projections are useful for containing and carrying fusion promoting substances other than bone such as bone morphogenetic proteins and genetic materials coding for the production of bone, or bone itself which could by way of example be in the form of a paste. It is further appreciated that for all the various embodiments of the surface configuration of the present invention, longitudinal grooves 130 can have horizontal cross-sections in a variety of configurations such as, without limitation, square-shaped or U-shaped configurations.

Figure 1B:
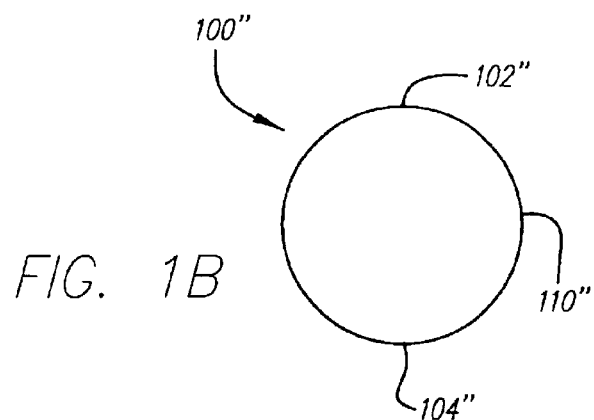
FIG. 1B is a top elevational view of an implant having a leading end, a trailing end, and sides forming a circle in accordance with an embodiment of the present invention.

Sequential projections can be positioned on an implant wherein each surface projection has forward facing facets facing the same direction such that consecutive projections are oriented forward facing facet to rearward facing facet. The lower most portion of the slope of the forward facing facet of a first surface projection in a sequence can be coincident with the rearward facet of the next surface projection in the sequence. Alternatively, the forward facet of a first surface projection and the rearward facet of the next surface projection in a sequence can be spaced apart and the space can be at least in part flat, curved, or any other surface configuration suitable for the intended use. The surface projections can be oriented relative to one another to form an array and are preferably geometrically disposed relative to one another in a pattern wherein at least a portion of the projection is aligned along a longitudinal, horizontal, diagonal, or curved line. Further, it is appreciated that the surface of the present invention can be useful with spinal implants of various configurations, including configurations wherein at least one of leading end, trailing end, and sides of the spinal implant is curved. By way of example and not limitation, the leading end, trailing end, and sides of the spinal implant can form an oval, an oblong, or a circle. For example, FIG. 1B shows an implant 100" having a leading end 102", a trailing end 104", and a sidewall 110" forming a circle. As shown in FIGS. 8–11, a second embodiment of the surface configuration of the present invention is generally referred to by the numeral 220. Surface configuration 220 includes surface projections 222 to facilitate insertion of implant 100 into an implantation site while resisting expulsion of implant 100 in a direction opposite to the direction of insertion. Each of surface projections 222 has an angled forward facet 224 directed at least in part toward leading end 202 of implant 100 and a rearward facet 226 directed at least in part toward trailing end 204 of implant 100. Forward facet 224 has a length greater than the length of rearward facet 226. Rearward facet 226 has a slope that is steeper than the slope of forward facet 224. In this embodiment, the base of rearward facet 226 forms an angle of approximately 45 degrees with respect to upper and/or lower surfaces 206, 208 of implant 100. Each one of surface projections 222 has a left side facet 232 and a right side facet 234 directed toward the sides of implant 100, and forward facet 224 and rearward facet 226.

In this embodiment of surface configuration 220, longitudinal grooves 230 have a V-shaped horizontal cross-section. The lower most portions of left and right side facets 232, 234 of consecutive side-by-side projections 222 can be coincident with each other or may be spaced apart, any space therebetween can be at least in part flat, curved, sloped or otherwise configured. Each surface projection has left and right side facets 232, 234 that converge to form a high point or peak 236 at the top of each surface projections 222. Each peak 236 can be aligned along lines that are perpendicular, parallel, and/or diagonally oriented to the longitudinal axis L of implant 100. The left and right side facets 232, 234 resist side-to-side motion of implant 100 after it is inserted into the implantation space. Peaks 236 engage the bone of the vertebral bodies adjacent to implant 100 in the implantation site.

As shown in FIGS. 12–15, a third embodiment of the surface configuration of the present invention is generally referred to by the numeral 320 is shown. Surface configuration 320 includes surface projections 322 to facilitate insertion of implant 100 into an implantation site while resisting expulsion of implant 100 in a direction opposite to the direction of insertion. Each of surface projections 322 has an angled forward facet 324 directed at least in part toward leading end 302 of implant 100 and a rearward facet 326 directed at least in part toward trailing end 304 of implant 100. Forward facet 324 has a length greater than the length of rearward facet 326. Rearward facet 326 has a slope that is steeper than the slope of forward facet 324. In this embodiment, the base of rearward facet 326 is "back cut" to form an angle greater than 90 degrees with respect to upper and/or lower surfaces 306, 308 of implant 100. The configuration of rearward facet 326 further enhances resistance of motion of the implant in a direction opposite to the direction of insertion. It is appreciated that the angle of the base of rearward facet 326 with respect to upper and/or lower surfaces 306, 308 of implant 100 can be any other angle suitable for the intended purpose of the present invention. Each one of surface projections 322 has a left side facet 332 and a right side facet 334 directed toward the sides of implant 100, and a forward facet 324 and a rearward facet 326.

In this embodiment of surface configuration 320, longitudinal grooves 330 have a V-shaped horizontal cross section. The lower most portions of left and right side facets 332, 334 of consecutive side-by-side projections 322 can be coincident with each other or may be spaced apart, and any space therebetween can be at least in part flat, curved, sloped or otherwise configured. Each surface projection 322 has left and right side facets 332, 334 that converge to form a high point or peak 336 at the top of each surface projection 322. Each peak 336 can be aligned along lines that are perpendicular, parallel, and/or diagonally oriented to the longitudinal axis L of implant 100. The left and right side facets 332, 334 resist side-to-side motion of implant 100 after it is inserted into the implantation space. Peaks 336 engage the bone of vertebral bodies V adjacent to implant 100 in the implantation site.

As shown in FIGS. 16–19B, a fourth embodiment of the surface configuration of the present invention is generally referred to by the numeral 420. Surface configuration 420 includes surface projections 422 configured to facilitate insertion of implant 100 in the direction of insertion into an implantation site while resisting expulsion of implant 100 in a direction opposite to the direction of insertion. Each of surface projections 422 has an angled forward facet 424 directed toward leading end 402 of implant 100 and a rearward portion 426 directed toward trailing end 404 of implant 100. Forward facet 424 has a length greater than the length of rearward portion 426. Rearward portion 426 has a slope that is steeper than the slope of forward facet 424. In this embodiment, the base of rearward portion 426 forms an angle of approximately 90 degrees or less with respect to upper and/or lower surfaces 406, 408 of implant 100. Rearward portion 426 can be a portion of surface projection 422, such as a facet, an edge, or a line for example. Each one of surface projections 422 has a left side forward facet 450, a right side forward facet 452, a left side rearward facet 454, and a right side rearward facet 456 directed toward the front and sides, and directed toward the rear and sides of implant 100, respectively, and forward facet 424 and rearward portion 426.

Surface configuration 420 can further include a second plurality of surface projections 460 having at least a left forward side facet 462 and a right forward side facet 464 directed at least in part toward leading end 402 and sides of implant 100, respectively, and at least one rearward facet 466 directed at least in part toward trailing end 400. In this embodiment, rearward facet 466 is approximately perpendicular to at least one of upper and lower surfaces 406, 408 of implant 100. Reward facet 466 may also be at an angle that is greater than or less than 90 degrees to at least one of upper and lower surfaces 406, 408 of implant 100. Left and right forward side facets 462, 464 have at least a first portion in a plane at an angle to the longitudinal axis of implant 100. Second surface projections 460 can be interspersed with surface projections 422.

Surface configuration 420 can further comprise a third plurality of surface projections 470 having at least a left rearward side facet 472 and a right rearward side facet 474 directed at least in part toward trailing end 404 and sides of implant 100, respectively, and at least one forward facet 476 directed at least in part toward leading end 402. In this embodiment, forward facet 476 is at an angle that is less than 90 degrees to at least one of upper and lower surfaces 406, 408 of implant 100. Forward facet 476 may also be approximately perpendicular to at least one of upper and lower surfaces 406, 408 of implant 100. Left and right rearward side facets 472, 474 have at least a first portion in a plane at an angle to the longitudinal axis of implant 100. Third surface projections 470 can be interspersed with surface projections 422 and/or second surface projections 460. Surface projections 422 may have a length approximating the combined length of second surface projections 460 and third surface projections 470.

In this embodiment, surface configuration 420 has angled grooves 440a–k that form a plurality of surface projections 422. In this example, angled grooves 440a–k are formed at an angle that is approximately 45 degrees to longitudinal axis L of spinal implant 100 and in this example, angled grooves 440a–k are approximately 90 degrees to one another. The angled grooves 440a–k can be formed, if machined, by first passing a cutting element at a 45 degree angle to the longitudinal axis L of implant 100 and then passing the cutting element at a 90 degree angle to the path of the first pass of the cutting element, or otherwise formed by casting, molding, and other methods for forming a surface configuration. It is appreciated that angled grooves 400a–k can be formed at various angles to the longitudinal axis L of implant 100 and to each other. For example, such angles can be less than 180 degrees.

In this embodiment of surface configuration 420, angled grooves 440a–k have a V-shaped horizontal cross-section. Each surface projection 422 has left and right side facets 432 and 434 that are convergent and form a high point or peak 436 at the top of each surface projections 422. Each peak 436 can be aligned along lines that are horizontally, longitudinally, and/or diagonally oriented along implant 100. The left and right side forward and rearward facets 450, 452, 454, 456 function to prevent side-to-side motion of implant 100 after it is inserted into the implantation space. Peaks 436 may also function like teeth to engage the bone of vertebral bodies V adjacent to the implant in the implantation site.

FIG. 19B shows a variation of second and third surface projections 460', 470' that can be cleaved in one or more directions to increase the number of exposed sides of each projection and thus increase the surface area of the implant bone engaging surface available to contact the bone of the vertebral bodies. A preferred embodiment of this variation of the second and third surface projections 460', 470' are cleaved by a longitudinal groove.

As shown in FIGS. 20–23, a fifth embodiment of the surface configuration of the present invention is generally referred to by the numeral 520. Surface configuration 520 includes surface projections 522 to facilitate insertion of implant 100 into an implantation site while resisting expulsion of implant 100 in a direction opposite to the direction of insertion. Surface projections 522 can be cleaved in one or more directions to increase the number of exposed sides of each projection and thus increase the surface area of the implant bone engaging surface available to contact the bone of the vertebral bodies. For example, the surface projections can be cleaved by a longitudinal cut 540 generally parallel to the longitudinal axis L of implant 100 to form a surface projection having nine exposed sides. The surface projections may further be cleaved by a horizontal cut 542 generally perpendicular to the longitudinal axis L of implant 100 to form a surface projection having eighteen exposed sides. The cuts can penetrate the surface projection at a depth substantially equal to that of the height of the surface projections as measured from the upper or lower surfaces of the implant. The cuts can be oriented along at least one of the longitudinal axis of the implant, an axis perpendicular to the longitudinal axis of said implant, and an axis at an angle between the longitudinal axis and the axis perpendicular to the longitudinal axis of the implant. It is appreciated that cuts 540 and 542 may be formed as part of the molding process for forming the surface projections.

When cleaved by longitudinal cut 540 and horizontal cut 542, each of surface projections 522 has angled forward facet 524a, 524b directed at least in part toward leading end 502 of implant 100 and rearward facets 526a, directed at least in part toward trailing end 504 of implant 100. Forward facet 524 has a length greater than the length of rearward facet 526. Rearward facets 526a, 526b have a slope that is steeper than the slope of forward facets 524a, 524b. The cleaved portion of surface projection 522 can be spaced apart by a predetermined distance and the space can be at least in part flat, curved, or any other surface configuration suitable for the intended use. In this embodiment, the base of rearward facets 526a, 526b forms an angle of approximately 45 degrees with respect to upper and/or lower surfaces 506, 508 of implant 100. Each one of surface projections 522 has left side facets 532a, 532b and right side facets 534a, 534b directed toward the sides of implant 100, and forward facets 524a, 524b and rearward facet 526a, 526b. In this embodiment of surface configuration 520, longitudinal grooves 530 have a V-shaped horizontal cross-section and each surface projection 522 has left and right side facets 532a, 532b, 534a, 534b that converge toward one another. The left and right side facets 532a, 532b, 534a, 534b resist side-to-side motion of implant 100 after it is inserted into the implantation space. The surface configuration of the present invention can be formed by molding, machining or otherwise. A preferred surface configuration of the present invention may readily be machined by milling from side to side, across the upper and lower vertebral body engaging surfaces, surface projections. A milling machine with a cutting tool having an angled cutting face such as a V-shaped profile can then be run through the plurality of surface projections parallel to the longitudinal axis of the implant to form the above-described surface. In a preferred embodiment, the V-shaped cutting tool of the milling machine has faces with an angle of approximately 90 degrees, which faces are at a 45-degree angle to the plane of the surfaces being so machined. Without departing from the present invention, the angle of the cutting faces can be more or less than 90 degrees, the angle of the cutting face to the surface to be cut can be more or less than 45 degrees, and rather than running the cutter element parallel to the longitudinal axis of the implant, the cutting element may be run at an angle. By way of example only and not limitation, this angle may be at 45 degrees to the longitudinal axis of the implant and each surface projection can be formed by two grooves crossing the projections at a 90 degree angle to each other.

The spinal implants of the present invention are made of artificial or naturally occurring materials suitable for implantation in the human spine. The implants can comprise bone including, but not limited to, cortical bone, materials other than bone, such as metals including, but not limited to, titanium and its alloys or ASTM material, surgical grade plastics, plastic composites, ceramics, or other materials suitable for use as a spinal implant. The implants of the present invention can further comprise or be combined with bone growth promoting materials, including but not limited to, bone, bone morphogenetic proteins, hydroxyapatite, and genes coding for the production of bone. The implants can be treated with a bone growth promoting substance, can be a source of osteogenesis, or can be bioabsorbable at least in part. The implants of the present invention can be formed of a porous material.

The spinal implants of the present invention can be for the purpose of achieving fusion. The upper and lower surfaces of the fusion implants can include at least one opening, each in communication with the other, to permit for the growth of bone from vertebral body to adjacent vertebral body through the implant. The implant can have an internal chamber and may also have an access opening for accessing the internal chamber, in which case the implant can further have a cover such as a cap to close the access opening at least in part. For example, FIG. 1A shows an implant 100' having a leading end 102', a trailing end 104', a sidewall 110', and a cap 101'. Openings in the upper and lower surfaces of the implant can communicate with the internal chamber to permit further growth of bone from vertebral body to adjacent vertebral body through the implant. The internal chamber can contain bone growth promoting materials, including but not limited to, bone, bone morphogenetic proteins, hydroxyapatite, and genes coding for the production of bone. The implants of the present invention can be formed of a material that intrinsically participates in the growth of bone from one of the adjacent vertebral bodies to the other of the adjacent vertebral bodies.

While various embodiments of the present invention are presented by way of example only and not limitation, common to each of them, is that the configuration of the surface is based on a plurality of surface projections disposed in arrays, each surface projection comprising at least one leading facet and at least one opposing trailing facet, in which the leading facet has a length greater than the trailing facet and the trailing facet has a steeper slope than the slope of the leading facet. The surface configuration is located on at least a portion of one of the opposed vertebral body engaging surfaces of the spinal implant.

Figure 1C:
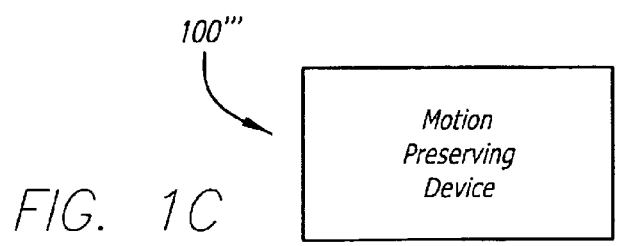
FIG. 1C is a graphical representation of a motion preserving device in accordance with an embodiment of the present invention.
Figure 18A:
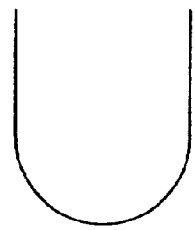
FIG. 18A is an enlarged fragmentary side view of a groove having a U-shape in accordance with an embodiment of the present invention from a view taken along area 18A of FIG. 18.
Figure 18B:
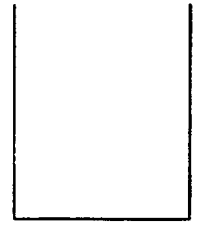
FIG. 18B is an enlarged fragmentary side view of a groove having a box-shape in accordance with an embodiment of the present invention from a view taken along area 18B of FIG. 18.
Figure 18C:
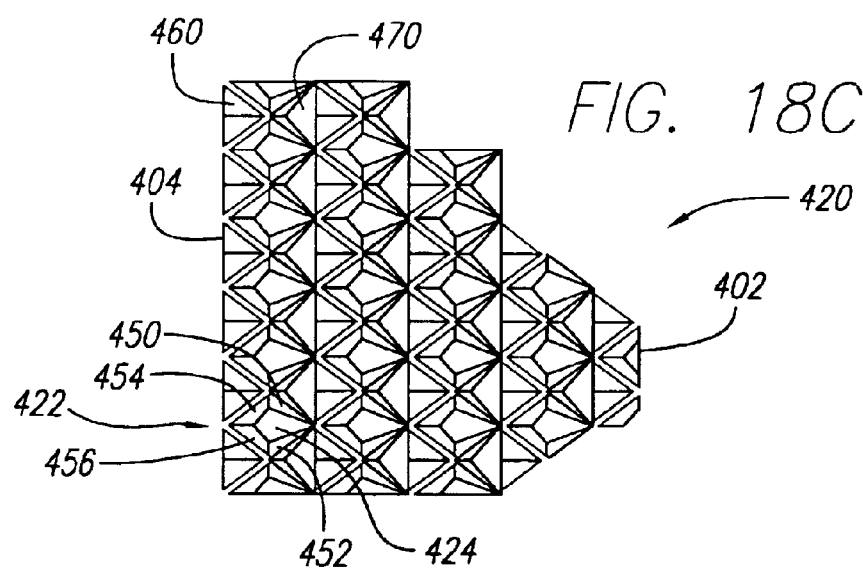
FIG. 18C is an enlarged fragmentary top plan view of a plurality of surface projections spaced apart from one another in accordance with an embodiment of the present invention.
Figure 24A:
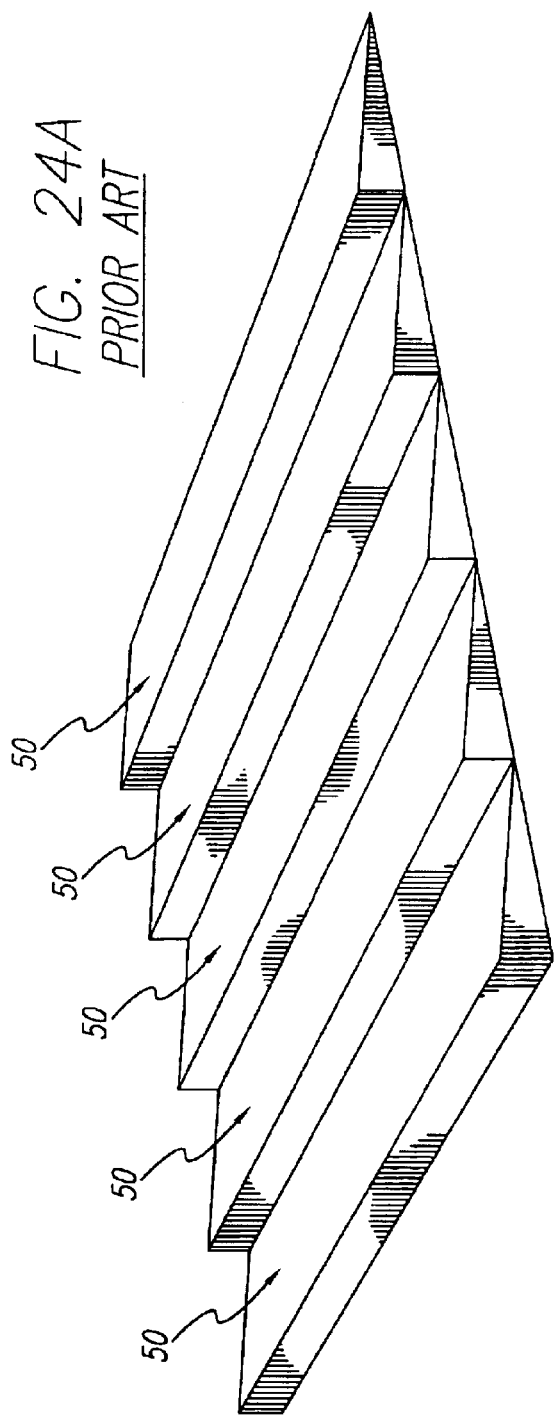
FIGS. 24A and 24B are perspective and side elevation views, respectively, of a prior art implant surface having forward facing ratchetings.
Figure 24B:
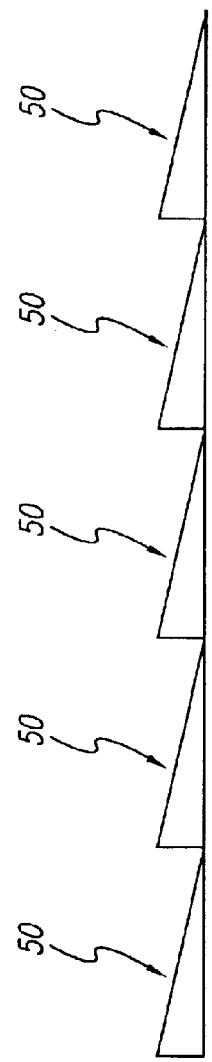

While the implant shown in FIGS. 1, 2, and 3 is an interbody spinal fusion implant, it is appreciated that the surface configuration of the present invention is applicable to any interbody spinal fusion implants, including but not limited to, an artificial disc or motion preserving device 100''' (FIG. 1C) having opposed surfaces incorporating the present inventive teachings for engaging each of the adjacent vertebral bodies.

It is believed that the operation and construction of the present invention will be apparent from the foregoing description and, while the invention shown and described herein has been characterized as particular embodiments, changes and modifications may be made therein without departing from the spirit and scope of the invention as defined in the following claim.

What is claimed is:

1. An interbody spinal implant for insertion between adjacent vertebral bodies of a human spine, said implant comprising:

a leading end for introduction of said spinal implant into the spine, an opposite trailing end, spaced apart sides therebetween, and a mid-longitudinal axis passing through said leading and trailing ends;

opposite upper and lower surfaces between said leading and trailing ends and said spaced apart sides, said upper surface adapted for placement in engagement with the bone of one of the vertebral bodies and said opposite lower surface adapted for placement toward the bone of the other of the vertebral bodies when said implant is placed between the adjacent vertebral bodies; and a plurality of surface projections formed on said upper and lower surfaces of said implant, said plurality of surface projections being adapted to engage bone, said plurality of surface projections including:

at least a first and a second surface projection each having a first facet configuration with at least one forward facing facet directed at least in part toward said leading end and at least one rearward portion directed at least in part toward said trailing end, said forward facet and said rearward portion having a length and a slope, the length of said forward facet being longer than the length of said rearward portion, the slope of said rearward portion being steeper than the slope of said forward facet, said first and second surface projections each having a peak along a first line that is transverse to the mid-longitudinal axis of said implant; and at least a third and a fourth surface projection each having a second facet configuration with at least one forward facet directed at least in part toward the leading end and at least one rearward portion directed at least in part toward the trailing end, said forward facet and said rearward portion of said second facet configuration having a length and a slope, the length of said forward facet of said second facet configuration being longer than the length of said rearward portion of said second facet configuration, the slope of said rearward portion of said second facet configuration being steeper than the slope of said forward facet of said second facet configuration, said third and fourth surface projections each having a peak along a second line that is transverse to the mid-longitudinal axis and off-set from the first line transverse to the mid-longitudinal axis, said second facet configuration of said third and fourth surface projections being different from said first facet configuration of said first and second surface projections.

2. The spinal implant of claim 1, wherein said rearward portion of each of said first and second surface projections is perpendicular to at least one of said upper and lower surfaces of said implant.

3. The spinal implant of claim 1, wherein said rearward portion of each of said first and second surface projections is at an angle to at least one of said upper and lower surfaces of said implant.

4. The spinal implant of claim 3, wherein said angle is less than 90 degrees.

5. The spinal implant of claim 1, wherein said forward facets of said first and second surface projections face the same direction.

6. The spinal implant of claim 1, wherein said first and second surface projections each include opposed side facets between said forward facet and said rearward portion, each of said side facets having at least a first portion in a plane passing through and being at an angle to the mid-longitudinal axis of said implant.

7. The spinal implant of claim 6, wherein said opposed side facets intersect each other.

8. The spinal implant of claim 1, wherein said peaks are aligned along lines that are at least one of parallel and diagonal to the mid-longitudinal axis of said implant.

9. The spinal implant of claim 6, wherein said side facets have a second portion passing through and being at an angle, wherein the angles of said first portion and said second portion are different.

10. The spinal implant of claim 1, wherein at least one of said surface projections includes a left forward side facet and a right forward side facet relative to the mid-longitudinal axis of said implant, said left forward side facet and said right forward side facet being directed toward said leading end and said sides, respectively, of said implant.

11. The spinal implant of claim 1, wherein at least one of said surface projections includes a left rearward side facet and a right rearward side facet relative to the mid-longitudinal axis of said implant, said left rearward side facet and said right rearward side facet being directed toward said trailing end and sides, respectively, of said implant.

12. The spinal implant of claim 10, wherein at least one of said surface projections includes a left rearward side facet and a right rearward side facet relative to the mid-longitudinal axis of said implant, said left rearward side facet and said right rearward side facet being directed toward said trailing end and sides, respectively, of said implant.

13. The spinal implant of claim 6, wherein adjacent side facets of adjacent surface projections are spaced apart to define a groove therebetween.

14. The spinal implant of claim 13, wherein a plurality of adjacent surface projections are spaced apart to form a plurality of grooves therebetween.

15. The spinal implant of claim 14, wherein at least one of said grooves is at an angle to the mid-longitudinal axis of said implant.

16. The spinal implant of claim 15, wherein said angle is less than 90 degrees to the mid-longitudinal axis of said implant.

17. The spinal implant of claim 15, wherein at least two of said grooves cross each other.

18. The spinal implant of claim 14, wherein at least one of said grooves has a horizontal cross-sectional shape selected from one of a v-shape, u-shape, and a box-like shape.

19. The spinal implant of claim 1, wherein said surface projections are oriented relative to one another to form an array.

20. The spinal implant of claim 1, wherein said surface projections are geometrically disposed relative to one another.

21. The spinal implant of claim 1, wherein said upper and lower surfaces of said implant are at least in part arcuate.

22. The spinal implant of claim 1, wherein at least one of said leading end, trailing end, and sides are curved.

23. The spinal implant of claim 1, wherein said sides are curved.

24. The spinal implant of claim 1, wherein each of said leading end, trailing end, and sides are curved.

25. The spinal implant of claim 24, wherein said leading end, trailing end, and sides form a circle.

26. The spinal implant of claim 1, wherein said upper and lower surfaces of said implant are at least in part planar.

27. The spinal implant of claim 1, wherein said upper and lower surfaces converge along the length of said implant.

28. The spinal implant of claim 1, wherein said implant comprises a material other than bone.

29. The spinal implant of claim 1, wherein said implant comprises bone.

30. The spinal implant of claim 29, wherein said bone includes cortical bone.

31. The spinal implant of claim 1, wherein said implant comprises bone growth promoting material.

32. The spinal implant of claim 31, wherein said bone growth promoting material is selected from one of bone morphogenetic protein, hydroxyapatite, and genes coding for the production of bone.

33. The spinal implant of claim 1, wherein said implant is treated with a bone growth promoting substance.

34. The spinal implant of claim 1, wherein said implant is a source of osteogenesis.

35. The spinal implant of claim 1, wherein said implant is at least in part bioabsorbable.

36. The spinal implant of claim 1, wherein said implant comprises metal.

37. The spinal implant of claim 36, wherein said metal is ASTM material suitable for use as a spinal fusion implant.

38. The implant of claim 36, wherein said metal includes titanium.

39. The implant of claim 1, wherein said implant comprises a plastic material.

40. The implant of claim 1, wherein said implant comprises a ceramic material.

41. The implant of claim 1, wherein said implant is formed of a porous material.

42. The implant of claim 1, wherein said implant is formed of a material that intrinsically participates in the growth of bone from one of the adjacent vertebral bodies to the other of the adjacent vertebral bodies.

43. The spinal implant of claim 1, wherein said implant is a motion preserving device adapted to space apart and allow motion between the adjacent vertebral bodies.

44. The spinal implant of claim 1, wherein said spinal implant is a fusion implant.

45. The spinal implant of claim 44, wherein said upper and lower surfaces include at least one opening to permit bone growth from one of the adjacent vertebral bodies to the other one of the adjacent vertebral bodies through said implant.

46. The spinal implant of claim 44, wherein said implant has an internal chamber and an access opening for accessing said internal chamber.

47. The spinal implant of claim 46, wherein said implant has a cap for closing said access opening.

48. The spinal implant of claim 46, wherein said upper and lower surfaces include at least one opening in communication with said internal chamber to permit bone growth from one of the adjacent vertebral bodies to the other one of the adjacent vertebral bodies through said implant.

49. The spinal implant of claim 46, wherein said internal chamber is capable of containing bone growth promoting material.

50. The spinal implant of claim 49, wherein said bone growth promoting material is selected from one of bone morphogenetic protein, hydroxyapatite, and genes coding for the production of bone.

51. The spinal implant of claim 1, further comprising at least one opening capable of retaining fusion promoting materials.

52. The spinal implant of claim 1, further comprising at least one cut cleaving said surface projection into at least two portions.

53. The spinal implant of claim 52, further comprising at least a second cut cleaving said surface projection into at least four portions.

54. The spinal implant of claim 52, where said cut penetrates said surface projection at a depth substantially equal to that of the height of said surface projection.

55. The spinal implant of claim 53, where said second cut penetrates said surface projection at a depth substantially equal to that of the height of said surface projection.

56. The spinal implant of claim 52, wherein said cut is oriented along one of the mid-longitudinal axis of said implant, an axis perpendicular to the mid-longitudinal axis of said implant, and an axis at an angle between the mid-longitudinal axis and the axis perpendicular to the mid-longitudinal axis of said implant.

57. The spinal implant of claim 1, wherein said second facet configuration further includes at least a left forward side facet and a right forward side facet directed at least in part toward said leading end and said sides, respectively, and at least one rearward facet directed at least in part toward said trailing end, said left and right forward side facets having at least a first portion in a plane passing through and being at an angle to the mid-longitudinal axis of said implant.

58. The spinal implant of claim 1, wherein said third and fourth surface projections are interspersed with said first and second surface projections.

59. The spinal implant of claim 57, further comprising at least a fifth and a sixth surface projection each having a third facet configuration with at least one forward facet directed at least in part toward the leading end and at least one rearward portion directed at least in part toward the trailing end, said forward facet and said rearward portion of said third facet configuration having a length and a slope, the length of said forward facet of said third facet configuration being longer than the length of said rearward portion of said third facet configuration, the slope of said rearward portion of said third facet configuration being steeper than the slope of said forward facet of said third facet configuration, said third facet configuration further including at least a left rearward side facet and a right rearward side facet directed at least in part toward said trailing end and said sides, respectively, said left and right rearward side facets having at least a first portion in a plane passing through and being at an angle to the mid-longitudinal axis of said implant.

60. The spinal implant of claim 59, wherein said fifth and sixth surface projections are interspersed with said first and second surface projections.

61. The spinal implant of claim 59, wherein said third, fourth, fifth, and sixth surface projections are interspersed with said first and second surface projections.

62. The spinal implant of claim 59, wherein one of said surface projections having said second facet configuration has a length approximating the combined length of two of said surface projections each having at least one of said first and third facet configurations.

63. The spinal implant of claim 1, further comprising at least a fifth and a sixth surface projection each having a third facet configuration with at least one forward facet directed at least in part toward the leading end and at least one rearward portion directed at least in part toward the trailing end, said forward facet and said rearward portion of said third facet configuration having a length and a slope, the length of said forward facet of said third facet configuration being longer than the length of said rearward portion of said third facet configuration, the slope of said rearward portion of said third facet configuration being steeper than the slope of said forward facet of said third facet configuration, said third facet configuration further including at least a left rearward side facet and a right rearward side facet directed at least in part toward said trailing end and said sides, respectively, said left and right rearward side facets having at least a first portion in a plane passing through and being at an angle to the mid-longitudinal axis of said implant.

64. An interbody spinal implant for insertion between adjacent vertebral bodies of a human spine, said implant comprising:

a leading end for introduction of said spinal implant into the spine, an opposite trailing end, spaced apart sides therebetween, and a mid-longitudinal axis passing through said leading and trailing ends;

opposite upper and lower surfaces between said leading and trailing ends and said spaced apart sides, said upper surface adapted for placement in engagement with the bone of one of the vertebral bodies and said opposite lower surface adapted for placement toward the bone of the other of the vertebral bodies when said implant is placed between the adjacent vertebral bodies; and a plurality of surface projections formed on said upper and lower surfaces of said implant, said plurality of surface projections being adapted to engage bone, said plurality of surface projections including:

at least a first and a second surface projection each having a first facet configuration with at least a left forward side facet and a right forward side facet directed at least in part toward said leading end and said sides, respectively, and a single rearward facet directed at least in part toward said trailing end, said left and right forward side facets having at least a first portion in a plane passing through and being at an angle to the mid-longitudinal axis of said implant, said first and second surface projections each having a peak along a first line that is transverse to the mid-longitudinal axis of said implant; and at least a third and a fourth surface projection each having a second facet configuration with at least one forward facet directed at least in part toward the leading end and at least one rearward portion directed at least in part toward the trailing end, said forward facet and said rearward portion of said second facet configuration having a length and a slope, the length of said forward facet of said second facet configuration being longer than the length of said rearward portion of said second facet configuration, the slope of said rearward portion of said second facet configuration being steeper than the slope of said forward facet of said second facet configuration, said third and fourth surface projections each having a peak along a second line that is transverse to the mid-longitudinal axis and off-set from the first line transverse to the mid-longitudinal axis, said second facet configuration of said third and fourth surface projections being different from said first facet configuration of said first and second surface projections.

65. The spinal implant of claim 64, wherein said second facet configuration includes opposed side facets between said forward facing facet and said rearward portion, said side facets having at least a first portion in a plane passing through and being at an angle to the mid-longitudinal axis of said implant.

66. The spinal implant of claim 64, wherein said third and fourth surface projections are interspersed with said first and second surface projections.

67. The spinal implant of claim 65, further comprising at least a fifth and a sixth surface projection each having a third facet configuration with at least one forward facet directed at least in part toward the leading end and at least one rearward portion directed at least in part toward the trailing end, said forward facet and said rearward portion of said third facet configuration having a length and a slope, the length of said forward facet of said third facet configuration being longer than the length of said rearward portion of said third facet configuration, the slope of said rearward portion of said third facet configuration being steeper than the slope of said forward facet of said third facet configuration, said third facet configuration further including at least a left rearward side facet and a right rearward side facet directed at least in part toward said trailing end and said sides, respectively, said left and right rearward side facets having at least a first portion in a plane passing through and being at an angle to the mid-longitudinal axis of said implant.

68. The spinal implant of claim 67, wherein said fifth and sixth surface projections are interspersed with said first and second surface projections.

69. The spinal implant of claim 67, wherein said third, fourth, fifth, and sixth surface projections are interspersed with said first and second surface projections.

70. The spinal implant of claim 67, wherein one of said surface projections having said second facet configuration has a length approximating the combined length of two of said surface projections each having at least one of said first and third facet configurations.

71. The spinal implant of claim 64, further comprising at least a fifth and a sixth surface projection each having a third facet configuration with at least one forward facet directed at least in part toward the leading end and at least one rearward portion directed at least in part toward the trailing end, said forward facet and said rearward portion of said third facet configuration having a length and a slope, the length of said forward facet of said third facet configuration being longer than the length of said rearward portion of said third facet configuration, the slope of said rearward portion of said third facet configuration being steeper than the slope of said forward facet of said third facet configuration, said third facet configuration further including at least a left rearward side facet and a right rearward side facet directed at least in part toward said trailing end and said sides, respectively, said left and right rearward side facets having at least a first portion in a plane passing through and being at an angle to the mid-longitudinal axis of said implant.

72. The spinal implant of claim 64, wherein said second facet configuration includes opposed side facets directed generally toward said sides of said implant, said side facets located between said forward facet and said rearward portion of said surface projections, said side facets converging toward each other in a direction away from the base of each of said third and fourth surface projections.

73. The spinal implant of claim 64, wherein said rearward facet is perpendicular to at least one of said upper and lower surfaces of said implant.

74. The spinal implant of claim 64, wherein said rearward facet is at an angle to at least one of said upper and lower surfaces of said implant.

75. The spinal implant of claim 74, wherein said angle is less than 90 degrees.

76. The spinal implant of claim 64, wherein said rearward facets of said first and second surface projections face the same direction.

77. The spinal implant of claim 64, wherein said left and right forward side facets intersect each other.

78. The spinal implant of claim 64, wherein adjacent left and right forward side facets of adjacent surface projections are spaced apart to define a groove therebetween.

79. The spinal implant of claim 64, wherein said surface projections are oriented relative to one another to form an array.

80. The spinal implant of claim 64, wherein said surface projections are geometrically disposed relative to one another.

81. The spinal implant of claim 64, wherein said upper and lower surfaces of said implant are at least in part planar.

82. The spinal implant of claim 64, wherein said upper and lower surfaces converge along the length of said implant.

83. The spinal implant of claim 64, wherein said implant comprises a material other than bone.

84. The spinal implant of claim 64, wherein said implant comprises bone.

85. The spinal implant of claim 84, wherein said bone includes cortical bone.

86. The spinal implant of claim 64, wherein said implant comprises bone growth promoting material.

87. The spinal implant of claim 86, wherein said bone growth promoting material is selected from one of bone morphogenetic protein, hydroxyapatite, and genes coding for the production of bone.

88. The spinal implant of claim 64, wherein said implant is at least in part bioabsorbable.

89. The spinal implant of claim 64, wherein said implant is a motion preserving device adapted to space apart and allow motion between the adjacent vertebral bodies.

90. The spinal implant of claim 64, wherein said upper and lower surfaces include at least one opening to permit bone growth from one of the adjacent vertebral bodies to the other one of the adjacent vertebral bodies through said implant.

91. The spinal implant of claim 64, further comprising at least one cut cleaving said surface projection into at least two portions.

92. The spinal implant of claim 91, where said cut penetrates said surface projection at a depth substantially equal to that of the height of said surface projection.

93. An interbody spinal implant for insertion between adjacent vertebral bodies of a human spine, said implant comprising:
  a leading end for introduction of said spinal implant into the spine, an opposite trailing end, spaced apart sides therebetween, and a mid-longitudinal axis passing through said leading and trailing ends;
  opposite upper and lower surfaces between said leading and trailing ends and said spaced apart sides, said upper surface adapted for placement in engagement with the bone of one of the vertebral bodies and said opposite lower surface adapted for placement toward the bone of the other of the vertebral bodies when said implant is placed between the adjacent vertebral bodies; and
  a plurality of surface projections formed on said upper and lower surfaces of said implant, said plurality of surface projections being adapted to engage bone, said plurality of surface projections including:
    at least a first and a second surface projection each having a first facet configuration with at least a left rearward side facet and a right rearward side facet directed at least in part toward said trailing end and said sides, respectively, and a single forward facet directed at least in part toward said leading end, said left and right rearward side facets having at least a first portion in a plane at an angle to the mid-longitudinal axis of said implant; and
    at least a third and a fourth surface projection each having a second facet configuration with at least one forward facet directed at least in part toward the leading end and at least one rearward portion directed at least in part toward the trailing end, said forward facet and said rearward portion of said second facet configuration having a length and a slope, the length of said forward facet of said second facet configuration being longer than the length of said rearward portion of said second facet configuration, the slope of said rearward portion of said second facet configuration being steeper than the slope of said forward facet of said second facet configuration, said third and fourth surface projections each having a peak along a second line that is transverse to the mid-longitudinal axis and off-set from the first line transverse to the mid-longitudinal axis, the second facet configuration of the third and fourth surface projections being different from the first facet configuration of the first and second surface projections.

94. The spinal implant of claim 93, wherein said second facet configuration includes opposed side facets between said forward facet and said rearward portion, said side facets having at least a first portion in a plane passing through and being at an angle to the mid-longitudinal axis of aid implant.

95. The spinal implant of claim 93, wherein said third and fourth surface projections are interspersed with said first and second surface projections.

96. The spinal implant of claim 94, further comprising at least a fifth and a sixth surface projection each having a third facet configuration with at least one forward facet directed at least in part toward the leading end and at least one rearward portion directed at least in part toward the trailing end, said forward facet and said rearward portion of said third facet configuration having a length and a slope, the length of said forward facet of said third facet configuration being longer than the length of said rearward portion of said third facet configuration, the slope of said rearward portion of said third facet configuration being steeper than the slope of said forward facet of said third facet configuration, said third facet configuration further including at least a left forward side facet and a right forward side facet directed at least in part toward said leading end and said sides, respectively, and a single rearward facet directed at least in part toward said trailing end, said left and right forward side facets having at least a first portion in a plane passing through and being at an angle to the mid-longitudinal axis of said implant.

97. The spinal implant of claim 96, wherein said fifth and sixth surface projections are interspersed with said first and second surface projections.

98. The spinal implant of claim 96, wherein said third, fourth, fifth, and sixth surface projections are interspersed with said first and second surface projections.

99. The spinal implant of claim 96, wherein one of said surface projections having said second facet configuration has a length approximating the combined length of two surface projections each having at least one of said first and third facet configurations.

100. The spinal implant of claim 93, further comprising at least a fifth and a sixth surface projection each having a third facet configuration with at least one forward facet directed at least in part toward the leading end and at least one rearward portion directed at least in part toward the trailing end, said forward facet and said rearward portion of said third facet configuration having a length and a slope, the length of said forward facet of said third facet configuration being longer than the length of said rearward portion of said third facet configuration, the slope of said rearward portion of said third facet configuration being steeper than the slope of said forward facet of said third facet configuration, said third facet configuration further including at least a left forward side facet and a right forward side facet directed at least in part toward said leading end and said sides, respectively, and a single rearward facet directed at least in part toward said trailing end, said left and right forward side facets having at least a first portion in a plane passing through and being at an angle to the mid-longitudinal axis of said implant.

101. The spinal implant of claim 93, wherein said second facet configuration includes opposed side facets directed generally toward said sides of said implant, said side facets located between said forward facet and said rearward portion of said surface projections, said side facets converging toward each other in a direction away from the base of each of said third and fourth surface projections.

102. The spinal implant of claim 93, wherein said forward facets of said first and second surface projections face the same direction.

103. The spinal implant of claim 93, wherein said forward facet of each of said first and second surface projections is at an angle to at least one of said upper and lower surfaces of said implant.

104. The spinal implant of claim 103, wherein said angle is less than 90 degrees.

105. The spinal implant of claim 93, wherein said left and right rearward side facets intersect each other.

106. The spinal implant of claim 93, wherein adjacent left and right rearward side facets of adjacent surface projections are spaced apart to define a groove therebetween.

107. The spinal implant of claim 93, wherein said surface projections are oriented relative to one another to form an array.

108. The spinal implant of claim 93, wherein said surface projections are geometrically disposed relative to one another.

109. The spinal implant of claim 93, wherein said upper and lower surfaces of said implant are at least in part planar.

110. The spinal implant of claim 93, wherein said upper and lower surfaces converge along the length of said implant.

111. The spinal implant of claim 93, wherein said implant comprises a material other than bone.

112. The spinal implant of claim 93, wherein said implant comprises bone.

113. The spinal implant of claim 112, wherein said bone includes cortical bone.

114. The spinal implant of claim 93, wherein said implant comprises bone growth promoting material.

115. The spinal implant of claim 114, wherein said bone growth promoting material is selected from one of bone morphogenetic protein, hydroxyapatite, and genes coding for the production of bone.

116. The spinal implant of claim 93, wherein said implant is at least in part bioabsorbable.

117. The spinal implant of claim 93, wherein said implant is a motion preserving device adapted to space apart and allow motion between the adjacent vertebral bodies.

118. The spinal implant of claim 93, wherein said upper and lower surfaces include at least one opening to permit bone growth from one of the adjacent vertebral bodies to the other one of the adjacent vertebral bodies through said implant.

119. The spinal implant of claim 93, further comprising at least one cut cleaving said surface projection into at least two portions.

120. The spinal implant of claim 119, where said cut penetrates said surface projection at a depth substantially equal to that of the height of said surface projection.

121. An interbody spinal implant for insertion between adjacent vertebral bodies of a human spine, said implant comprising:

a leading end for introduction of said spinal implant into the spine, an opposite trailing end, spaced apart sides therebetween, and a mid-longitudinal axis passing through said leading and trailing ends;

opposite upper and lower surfaces between said leading and trailing ends and said spaced apart sides, said upper surface adapted for placement in engagement with the bone of one of the vertebral bodies and said opposite lower surface adapted for placement toward the bone of the other of the vertebral bodies when said implant is placed between the adjacent vertebral bodies;

at least a first and a second surface projection formed on said upper and lower surfaces, each of said first and second surface projections having at least one forward facing facet directed at least in part toward said leading end and at least one rearward portion directed at least in part toward said trailing end, said forward facet and said rearward portion having a length and a slope, the length of said forward facet being longer than the length of said rearward portion, the slope of said rearward portion being steeper than the slope of said forward facet, said projections having a left forward side facet and a right forward side facet directed toward said leading end and said sides, respectively, of said implant, each of said left forward and right forward side facets having at least a first portion in a plane passing through and being at an angle to the mid-longitudinal axis of said implant;

at least a third and a fourth surface projection formed on said upper and lower surfaces, each of said third and fourth surface projections having at least a left forward side facet and a right forward side facet directed at least in part toward said leading end and said sides, respectively, and a single rearward facet directed at least in part toward said trailing end, said left and right forward side facets having at least a first portion in a plane passing through and being at an angle to the mid-longitudinal axis of said implant; and at least a fifth and a sixth surface projection formed on said upper and lower surfaces, each of said fifth and sixth surface projections having at least a left rearward side facet and a right rearward side facet directed at least in part toward said trailing end and said sides, respectively, and a single forward facet directed at least in part toward said leading end, said left and right rearward side facets having at least a first portion in a plane passing through and being at an angle to the mid-longitudinal axis of said implant.

122. The spinal implant of claim 121, wherein said rearward facet of said third and fourth surface projections is perpendicular to at least one of said upper and lower surfaces of said implant.

123. The spinal implant of claim 121, wherein said rearward portion of said first and second surface projections is at an angle to at least one of said upper and lower surfaces of said implant.

124. The spinal implant of claim 123, wherein said angle is less than 90 degrees.

125. The spinal implant of claim 123, wherein said forward facets of said first and second surface projections face the same direction.

126. The spinal implant of claim 121, wherein said left and right forward side facets of said third and fourth surface projections intersect each other.

127. The spinal implant of claim 126, wherein said left and right forward side facets of said third and fourth surface projections converge to form a peak at the top of each of said third and fourth surface projections.

128. The spinal implant of claim 127, wherein said peaks are aligned along lines that are at least one of perpendicular, parallel, and diagonal to the mid-longitudinal axis of said implant.

129. The spinal implant of claim 121, wherein said first and second surface projections have a second portion in a plane passing through and being at an angle to the mid-longitudinal axis, wherein the angles of said first portion and said second portion are different.

130. The spinal implant of claim 121, wherein rearward facets of said third and fourth surface projections face the same direction.

131. The spinal implant of claim 121, wherein each of said first and second surface projections includes a left rearward side facet and a right rearward side facet directed toward said trailing end and sides, respectively, of said implant.

132. The spinal implant of claim 121, wherein each of said first and second surface projections includes at least five facets.

133. The spinal implant of claim 121, wherein adjacent side facets of said first and second surface projections are spaced apart to define a groove therebetween.

134. The spinal implant of claim 133, wherein a plurality of adjacent surface projections are spaced apart to form a plurality of grooves therebetween.

135. The spinal implant of claim 134, wherein at least one of said grooves is at an angle to the mid-longitudinal axis of said implant.

136. The spinal implant of claim 135, wherein said angle is less than 90 degrees to the mid-longitudinal axis of said implant.

137. The spinal implant of claim 135, wherein at least two of said grooves cross each other.

138. The spinal implant of claim 134, wherein at least one of said grooves has a horizontal cross-sectional shape selected from one of a v-shape, u-shape, and a box-like shape.

139. The spinal implant of claim 121, wherein said upper and lower surfaces of said implant are at least in part arcuate.

140. The spinal implant of claim 121, wherein said upper and lower surfaces of said implant are at least in part planar.

141. The spinal implant of claim 121, wherein said upper and lower surfaces converge along the length of said implant.

142. The spinal implant of claim 121, wherein said upper and lower surfaces include at least one opening to permit bone growth from one of the adjacent vertebral bodies to the other one of the adjacent vertebral bodies through said implant.

143. The spinal implant of claim 121, wherein said implant has an internal chamber and an access opening for accessing said internal chamber.

144. The spinal implant of claim 121, wherein said third, fourth, fifth, and sixth surface projections are interspersed with said first and second surface projections.

145. The spinal implant of claim 121, wherein each of said first and second surface projections have a length approximating the combined length of one of said third and fourth surface projections and one of said fifth and sixth surface projections.

146. The spinal implant of claim 121, wherein said forward facets of each of said fifth and sixth surface projections face the same direction.

147. The spinal implant of claim 121, wherein said forward facets of each of said fifth and sixth surface projections is at an angle to at least one of said upper and lower surfaces of said implant.

148. The spinal implant of claim 147, wherein said angle is less than 90 degrees.

149. The spinal implant of claim 121, wherein said left and right rearward side facets of each of said fifth and sixth surface projections intersect each other.

150. The spinal implant of claim 121, wherein adjacent left and right rearward side facets of said fifth and sixth surface projections are spaced apart to define a groove therebetween.

151. The spinal implant of claim 121, wherein said implant is made at least in part of bone.

152. The spinal implant of claim 121, wherein said implant is made at least in part of a metal.

153. The spinal implant of claim 121, in combination with a fusion promoting substance.

154. The spinal implant of claim 153, wherein said fusion promoting substance includes at least one of bone morphogenetic protein, hydroxyapatite, genes coding for the production of bone, and bone.

155. The spinal implant of claim 1, in combination with a fusion promoting substance.

156. The spinal implant of claim 155, wherein said fusion promoting substance includes at least one of bone morphogenetic protein, hydroxyapatite, genes coding for the production of bone, and bone.

157. The spinal implant of claim 64, in combination with a fusion promoting substance.

158. The spinal implant of claim 157, wherein said fusion promoting substance includes at least one of bone morphogenetic protein, hydroxyapatite, genes coding for the production of bone, and bone.

159. The spinal implant of claim 93, in combination with a fusion promoting substance.

160. The spinal implant of claim 159, wherein said fusion promoting substance includes at least one of bone morphogenetic protein, hydroxyapatite, genes coding for the production of bone, and bone.

161. The spinal implant of claim 1, further comprising at least a fifth and a sixth surface projection each having a third facet configuration with at least one forward facet directed at least in part toward the leading end and at least one rearward portion directed at least in part toward the trailing end, said forward facet and said rearward portion of said third facet configuration having a length and a slope, the length of said forward facet of said third facet configuration being longer than the length of said rearward portion of said third facet configuration, the slope of said rearward portion of said third facet configuration being steeper than the slope of said forward facet of said third facet configuration, said fifth and sixth surface projections each having a peak along a third line that is transverse to the mid-longitudinal axis and off-set from the first and second lines, said third facet configuration of said fifth and sixth surface projections being different from said first facet configuration of said first and second surface projections and said second facet configuration of said third and fourth surface projections.

162. The spinal implant of claim 1, wherein at least one of said surface projections along the first line have a maximum height from one of said upper and lower surfaces of said implant that is substantially the same as the maximum height of one of said surface projections along the second line.

163. The spinal implant of claim 1, wherein said implant includes at least three surface projections having said first facet configuration along the first line and at least three surface projections having said second facet configuration along the second line.

164. The spinal implant of claim 1, wherein said implant includes at least four surface projections having said first facet configuration along the first line and at least four surface projections having said second facet configuration along the second line.

165. The spinal implant of claim 1, wherein said implant includes at least five surface projections having said first facet configuration along the first line and at least five surface projections having said second facet configuration along the second line.

166. The spinal implant of claim 64, further comprising at least a fifth and a sixth surface projection each having a third facet configuration with at least one forward facet directed at least in part toward the leading end and at least one rearward portion directed at least in part toward the trailing end, said forward facet and said rearward portion of said third facet configuration having a length and a slope, the length of said forward facet of said third facet configuration being longer than the length of said rearward portion of said third facet configuration, the slope of said rearward portion of said third facet configuration being steeper than the slope of said forward facet of said third facet configuration, said fifth and sixth surface projections each having a peak along a third line that is transverse to the mid-longitudinal axis and off-set from the first and second lines, said third facet configuration of said fifth and sixth surface projections being different from said first facet configuration of said first and second surface projections and said second facet configuration of said third and fourth surface projections.

167. The spinal implant of claim 64, wherein at least one of said surface projections along the first line have a maximum height from one of said upper and lower surfaces of said implant that is substantially the same as the maximum height of one of said surface projections along the second line.

168. The spinal implant of claim 64, wherein said implant includes at least three surface projections having said first facet configuration along the first line and at least three surface projections having said second facet configuration along the second line.

169. The spinal implant of claim 64, wherein said implant includes at least four surface projections having said first facet configuration along the first line and at least four surface projections having said second facet configuration along the second line.

170. The spinal implant of claim 64, wherein said implant includes at least five surface projections having said first facet configuration along the first line and at least five surface projections having said second facet configuration along the second line.

171. The spinal implant of claim 93, further comprising at least a fifth and a sixth surface projection each having a third facet configuration with at least one forward facet directed at least in part toward the leading end and at least one rearward portion directed at least in part toward the trailing end, said forward facet and said rearward portion of said third facet configuration having a length and a slope, the length of said forward facet of said third facet configuration being longer than the length of said rearward portion of said third facet configuration, the slope of said rearward portion of said third facet configuration being steeper than the slope of said forward facet of said third facet configuration, said fifth and sixth surface projections each having a peak along a third line that is transverse to the mid-longitudinal axis and off-set from the first and second lines, said third facet configuration of said fifth and sixth surface projections being different from said first facet configuration of said first and second surface projections and said second facet configuration of said third and fourth surface projections.

172. The spinal implant of claim 93, wherein at least one of said surface projections along the first line have a maximum height from one of said upper and lower surfaces of said implant that is substantially the same as the maximum height of one of said surface projections along the second line.

173. The spinal implant of claim 93, wherein said implant includes at least three surface projections having said first facet configuration along the first line and at least three surface projections having said second facet configuration along the second line.

174. The spinal implant of claim 93, wherein said implant includes at least four surface projections having said first facet configuration along the first line and at least four surface projections having said second facet configuration along the second line.

175. The spinal implant of claim 93, wherein said implant includes at least five surface projections having said first facet configuration along the first line and at least five surface projections having said second facet configuration along the second line.

176. The spinal implant of claim 121, wherein at least one of said surface projections along the first line have a maximum height from one of said upper and lower surfaces of said implant that is substantially the same as the maximum height of one of said surface projections along the second line.

* * * * *

UNITED STATES PATENT AND TRADEMARK OFFICE
CERTIFICATE OF CORRECTION

PATENT NO. : 6,827,740 B1
DATED : December 7, 2004
INVENTOR(S) : Gary K. Michelson It is certified that error appears in the above-identified patent and that said Letters Patent is hereby corrected as shown below:

Title page,
Item [56], References Cited, U.S. PATENT DOCUMENTS, insert the following:

| | | |
|---|---|---|
| --4,531,244 | 7/1985 | Hamas |
| 4,673,409 | 6/1987 | Van Kampen |
| 4,795,742 | 1/1989 | Crowinshield et al. |
| 4,955,907 | 9/1990 | Ledergerber |
| 5,716,412 | 2/1998 | DeCarlo Jr. et al. |
| 6,190,414 | 2/2001 | Young et al. |
| 2002/0068978 | 6/2002 | Camino et al. |
| 6,432,106 | 8/2002 | Fraser |
| 6,592,624 | 7/2003 | Fraser et al.--. |

Column 18,
Line 64, change "aid" to -- said --.

Signed and Sealed this

First Day of March, 2005

JON W. DUDAS
*Director of the United States Patent and Trademark Office*